United States Patent
Lacey et al.

(10) Patent No.: US 9,700,273 B2
(45) Date of Patent: Jul. 11, 2017

(54) SYSTEM AND METHOD FOR THERMAL MANAGEMENT OF A CT DETECTOR

(71) Applicant: General Electric Company, Schenectady, NY (US)

(72) Inventors: Joseph James Lacey, Waukesha, WI (US); Ashutosh Joshi, Waukesha, WI (US); Venkatarao Ryali, Bangalore (IN); Sanketh Bhat, Bangalore (IN)

(73) Assignee: General Electric Company, Schenectady, NY (US)

( * ) Notice: Subject to any disclaimer, the term of this patent is extended or adjusted under 35 U.S.C. 154(b) by 226 days.

(21) Appl. No.: 14/620,254

(22) Filed: Feb. 12, 2015

(65) Prior Publication Data

US 2016/0174920 A1 Jun. 23, 2016

(30) Foreign Application Priority Data

Dec. 18, 2014 (IN) .......................... 6361/CHE/2014

(51) Int. Cl.
*A61B 6/00* (2006.01)
*A61B 6/03* (2006.01)

(52) U.S. Cl.
CPC ............ *A61B 6/4488* (2013.01); *A61B 6/035* (2013.01); *A61B 6/4266* (2013.01)

(58) Field of Classification Search
CPC ........ A61B 6/4488; A61B 6/035; A61B 6/032
USPC ....................... 378/4–20, 199, 200
See application file for complete search history.

(56) References Cited

U.S. PATENT DOCUMENTS

| 7,102,308 B2 | 9/2006 | Lacey et al. |
| 8,699,660 B2 | 4/2014 | Joshi et al. |
| 2005/0287008 A1* | 12/2005 | Lacey .................. F04D 27/004 417/32 |
| 2006/0109956 A1* | 5/2006 | Lacey .................. A61B 6/035 378/199 |

* cited by examiner

*Primary Examiner* — Courtney Thomas
(74) *Attorney, Agent, or Firm* — Andrus Intellectual Property Law, LLP (57) ABSTRACT

In one embodiment, a system for thermal management in a CT device comprises first and second thermal management zones, each comprising an x-ray detector, at least one variable speed fan proximate to the x-ray detector, an air temperature sensor positioned to measure an air temperature of the intake air to the variable speed fan, a rail heater in thermal contact with the x-ray detector, a rail temperature sensor in thermal contact with the rail heater to measure a rail temperature, and a controller that controls the variable speed fan as a function of at least the air temperature and the rail heater as a function of the rail temperature to maintain a temperature of the x-ray detector within a predetermined range.

18 Claims, 8 Drawing Sheets

| Tset | Tair | dT | dT_base | Gain ratio |
|---|---|---|---|---|
| 40 | 36 | 4 | 10 | 2.5 |
| 40 | 35 | 5 | 10 | 2 |
| 40 | 34 | 6 | 10 | 1.666666667 |
| 40 | 33 | 7 | 10 | 1.428571429 |
| 40 | 32 | 8 | 10 | 1.25 |
| 40 | 31 | 9 | 10 | 1.111111111 |
| 40 | 30 | 10 | 10 | 1 |
| 40 | 29 | 11 | 10 | 0.909090909 |
| 40 | 28 | 12 | 10 | 0.833333333 |
| 40 | 27 | 13 | 10 | 0.769230769 |
| 40 | 26 | 14 | 10 | 0.714285714 |
| 40 | 25 | 15 | 10 | 0.666666667 |
| 40 | 24 | 16 | 10 | 0.625 |

FIG. 8

SYSTEM AND METHOD FOR THERMAL MANAGEMENT OF A CT DETECTOR

CROSS-REFERENCE TO RELATED APPLICATION

The present application is based on and claims priority to Indian Patent Application No. 6361/CHE/2014 filed Dec. 18, 2014, the disclosure of which is incorporated herein by reference.

BACKGROUND OF THE INVENTION

The present disclosure pertains to the art of medical diagnostic imaging, such as to computerized tomographic (CT) scanners. The disclosure finds particular application in conjunction with cooling systems associated with CT scanners and will be described with particular reference thereto. It will be appreciated, however, that the invention has broader applications and may be advantageously employed in other environments.

When a CT scanner is in operation, an X-ray beam rotates rapidly in a patient examination region. An X-ray tube rotates continuously around the examination region and causes the beam to so rotate. The X-ray tube generates a significant amount of heat as well as the X-rays. Because the x-ray sensors or detectors are heavily affected by absolute and temperature differences during calibration and scanning, a thermal control system is necessitated. X-ray sensors typically have 4 dominate temperature dependent properties that require tight temperature control systems: 1) Electronic gain temperature coefficient or gain shifts from the photo diode and A to D circuits, 2) offset drift of photo diode & A to D circuitry, which results in change of zero current reference during a scan, 3) Current leakage due to photo diode R shunt resistance which is a function of absolute temperature, and 4) Light output variation of scintillator material as function of temperature. These 4 temperature dependent properties translate into need for temperature control system to limit maximum photo diode temperature, minimal temperature change between calibration of the machine and scanning with machine, and lastly extremely small temperature change within a scan (data acquisition period). Failure to control absolute temperature and temperature change will result in image artifacts and loss of image resolution.

One available CT scanner cooling system uses an air conditioned sealed gantry to maintain radiation detectors at a proper working, temperature. CT scanner cooling systems of the type to which this invention pertains have included air conditioning units housed within CT scanner gantries. Other cooling systems employed in presently available imaging systems include liquid cooling systems and tight gantry system air temperature controls and/or electronic temperature correction schemes. Such cooling systems have been employed to cool radiation detectors, as well as other temperature-sensitive components associated with the CT scanners and other imaging devices.

The use of air conditioning systems in connection with CT scanners has several drawbacks. Gantry air conditioning systems are housed outside of the CT gantry due to size and audible noise of the air conditioning units. Typically the air conditioning units are vapor compression based or use hospital chilled water in a liquid to liquid heat exchange. These units add hardware cost, installation complexity, require significantly more electrical power in addition to CT scanner and increase overall system maintenance. Additionally vapor compression systems are significant audible noise sources and thus typically are placed outside of scan room further complicating siting of CT machine.

The use of liquid cooled gantries and/or electronic temperature correction schemes also have drawbacks, as they add complexity and cost to the system. Further, liquid cooling, systems add reliability issues, such as leakage problems. Temperature corrections, although favorable with respect to cost, induce loss of imaging accuracy.

Currently available data acquisition systems (DAS) cooling is also done with air cooled systems employing multiple fans. Such systems include that described in U.S. Pat. No. 7,102,308.

Thermal management of CT detector systems is required to prevent image artifacts or errors and to enable high quality images (improved signal to noise ratio) and for the life of the electronic components. As gantries become smaller and components more tightly integrated, coupled dynamics and flows inside a gantry become complicated and thermal management becomes more difficult. Thus, improved cooling systems are needed to provide sufficient control over the temperature for use in some imaging systems to maintain even and consistent temperature control and good image reconstruction quality.

SUMMARY OF THE INVENTION

In one embodiment, a system for thermal management in a CT device comprises first and second thermal management zones, each comprising an x-ray detector, at least one variable speed fan proximate to the x-ray detector, an air temperature sensor positioned to measure an air temperature of the intake air to the variable speed fan, a rail heater in thermal contact with the x-ray detector, a rail temperature sensor in thermal contact with the rail heater to measure a rail temperature, and a controller that controls the variable speed fan as a function of at least the air temperature and the rail heater as a function of the rail temperature to maintain a temperature of the x-ray detector within a predetermined range.

An embodiment of the temperature control method comprises measuring the temperature of a first device with a first device temperature sensor disposed in thermal contact with the first device, and disposing a first variable speed fan proximate to the first device. The method further includes measuring a first air temperature with a first air temperature sensor disposed proximate to the first variable speed fan, and measuring a first rail temperature with a first rail temperature sensor disposed in thermal contact with a first rail heater. A first controller is operated to control, the first variable speed fan as a function of the first air temperature and to control the first rail heater as a function of the first rail temperature to maintain the temperature of the first device within a predetermined range. The method further comprises measuring the temperature of a second device with a second device temperature sensor disposed in thermal contact with the second device, and disposing a second variable speed fan proximate to the second device. A second air temperature is measured with a second air temperature sensor disposed proximate to the second variable speed fan. A second rail temperature is measured with a second rail temperature sensor disposed in thermal contact with a second rail heater. A second controller is operated to control the second variable speed fan as a function of the second air temperature and to control the second rail heater as a function of the second rail temperature to maintain the temperature of the second device within the predetermined range. In the temperature control method, the first device and the second device are separated by a full partition preventing air from flowing between the first device and the second device.

An embodiment of a system for thermal management of arm imaging device has a housing defining at least two zones that are separated from each other, each zone having, at least one air inlet and air outlet. Each zone has at least a variable speed fan positioned near the air inlet, an air temperature sensor positioned to measure an air temperature of the intake air to the variable speed fan, an x-ray detector, a temperature sensor in thermal contact with the x-ray detector to measure the temperature of the x-ray detector, a rail heater in thermal contact with the x-ray detector, and a flow diverter that directs an output of the variable speed fan toward the x-ray detector. Each zone also comprises a controller that controls the variable speed fan as a function of at least the air temperature and the temperature of the x-ray detector and controls the rail heater as a function of at least the temperature of the x-ray detector to maintain a temperature of the x-ray detector within a predetermined range.

BRIEF DESCRIPTION OF THE DRAWINGS

The drawings illustrate the best mode presently contemplated of carrying out the disclosure. In the drawings.

DETAILED DESCRIPTION OF THE DRAWINGS

Figure 1:
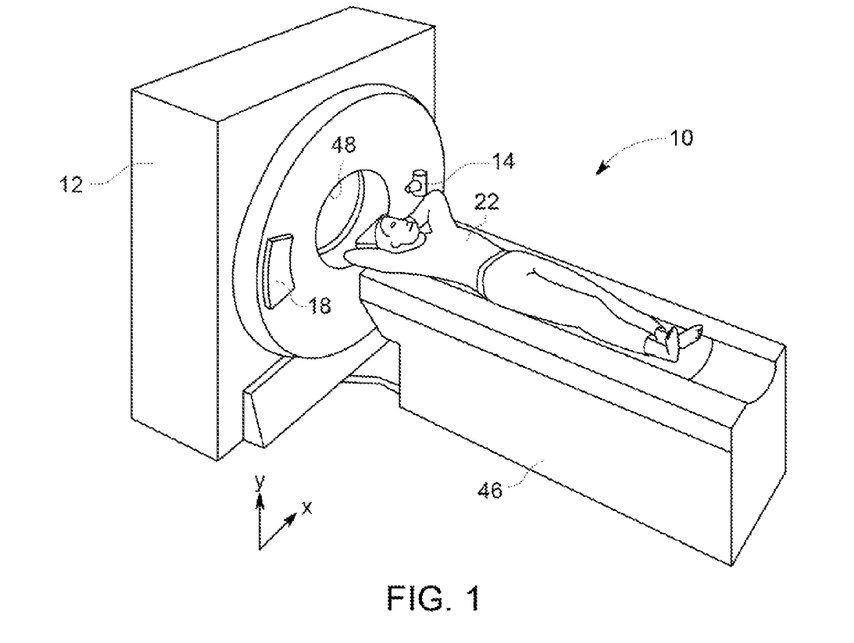
FIG. 1 depicts an exemplary CT imaging system.
Figure 2:
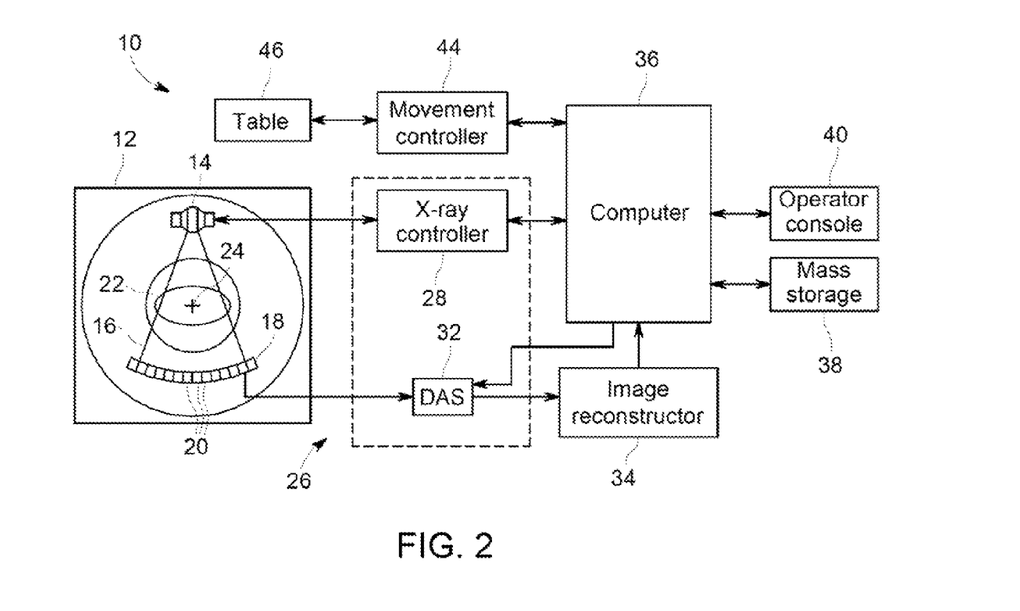
FIG. 2 provides a schematic diagram of an exemplary CT image system.

Referring to FIGS. 1 and 2, a computed tomography (CT) imaging system 10 is shown as including a gantry 12 representative of a CT scanner. The gantry 12 has an x-ray source 14 that projects a beam of x-rays 16 toward a detector array 18 on the opposite side of the gantry 12. The detector array 18 may be thrilled by a plurality of detection elements 20 which together sense the projected x-rays that pass through a medical patient 22. Furthermore, the detector array 18 may be broken into two or more sub-arrays, or detection sub-systems, which may employed together to create a single image. Each detection element 20 produces an electrical signal that represents the intensity of an impinging x-ray beam and hence, the attenuation of the beam as it passes through the patient 22. During a scan to acquire x-ray projection data, the gantry housing 12 and the components mounted thereon rotate about a center of gravity of axis 24.

The operation of the x-ray source 14 is governed by a control mechanism 26 of the CT system 10. The control mechanism 26 includes an x-ray controller 28 that provides power and timing signals to the x-ray source 14. A data acquisition system (DAS) 32 in the control mechanism 26 samples analog data from the detection elements 20 and converts the data to digital signals for subsequent processing. An image reconstructor 34 receives sampled and digitized x-ray data from the DAS 32 and performs high speed image reconstruction. The reconstructed image is applied as an input to a computer 36 which stores the image in a mass storage device 38.

The computer 36 also receives and supplies signals via a user interface or graphical user interface (GUI). Specifically, the computer 36 receives commands and scanning parameters from an operator console 40 that preferably includes one or more user interface devices, such as input mechanisms and/or display mechanisms. The operator supplied commands and parameters are used by the computer 36 to provide control signals and information to the x-ray controller 28, the DAS 32, and a table motor controller 44 in communication with a table 46 to control operation of and movement of the system components.

Figure 3:
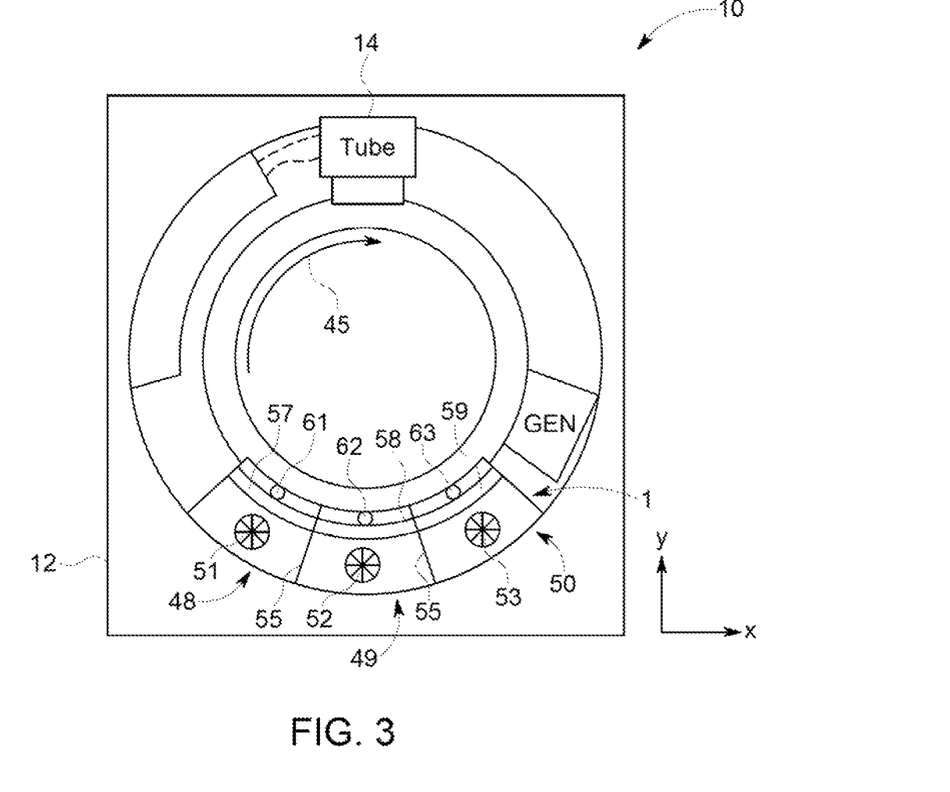
FIG. 3 provides an exemplary embodiment of a CT imaging system incorporating a system and method for thermal management of a detector device.

FIG. 3 illustrates a cross section view of gantry 12 in an X-Y plane relative to the perspective view of FIG. 1. Gantry 12 has an x-ray tube 14 that projects a beam of x-rays 16 (FIG. 2) toward detectors 57-59 on the opposite side of the gantry 12. Detectors 57-59 include an analog/digital (A/D) conversion circuitry (not shown) that heats up during operation and is cooled with a plurality of fans (3 shown) on the opposite side of gantry 12 proximate detectors 57-59. As gantry 12 rotates in a direction indicated generally with arrow 45, detectors 57-59 and a plurality of fans 51-53 rotate in the same direction.

More specifically, the CT imaging system 10 of FIG. 3 incorporates a system for thermal management 1 having a plurality of fans 51-53 associated with one or more detector devices 57-59. Also, three rail heaters 61-63 may be associated with the detectors 57-59, such as in a one-to-one ratio. Each detector 57-59 is housed in a separate zone 48-50, and each zone is separated by a flow partition 55 or is otherwise broken into independent flow streams. Each zone 48-50 is a thermal management zone separated by a flow partition 55 which prevents air flow between zones and also, in some embodiments, may be a thermal barrier preventing the flow of heat between zones 48-50. In this exemplary embodiment, zone one 48 has a variable speed fan positioned to blow air in order to cool detector 57. Rail heater 61 is positioned to generate heat in order to warm the detector 57. Accordingly, the system for thermal management utilizes the fan 51 and rail heater 61 to manage the temperature of the detector 57 in zone one 48. Likewise, in zone two 49 and zone three 50, variable speed fans 52 and 53 and rail heaters 62 and 63 are operated to manage the temperature of the detectors 58 and 59.

Each detector 57-59 may be a separate and independent detector array, or may be a detector sub-system comprising part of a larger detector, such as detector array 18 (FIG. 1). In other words, the detector devices 57-59 may each be subdetectors that, taken together, all comprise parts of a larger detector. In one embodiment, DAS 32 is operably coupled to each of the detectors 57-59. Each detector 57-59 may be any detector known in the art which may be suitable as an x-ray detector in an imaging device, such as a CT device.

In the exemplary embodiment of FIG. 3, each of the three zones 48-50 have a single variable speed fan 51-52. However, in other embodiments, a system for thermal management 1 may comprise two or more zones, up to n number of zones. The zones of various embodiments of the system for thermal management 1 may be of varying and differing sizes, shapes, volumes, etc. Further, each zone may comprise one or more variable speed fans, up to n number of fans.

Figure 4A:
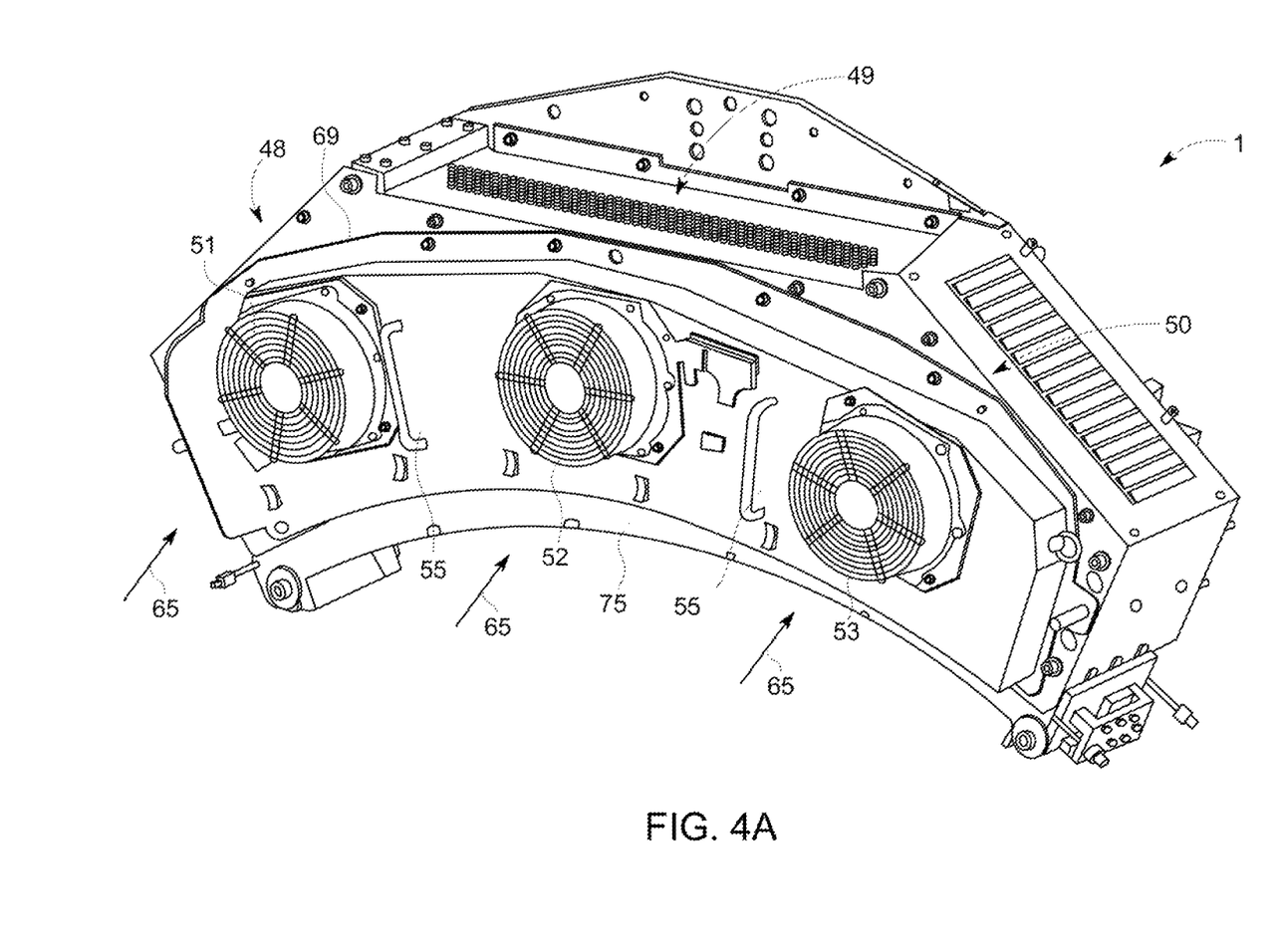
FIGS. 4a and 4b provide external front and back views of an embodiment of a system for thermal management of a device.
Figure 4B:
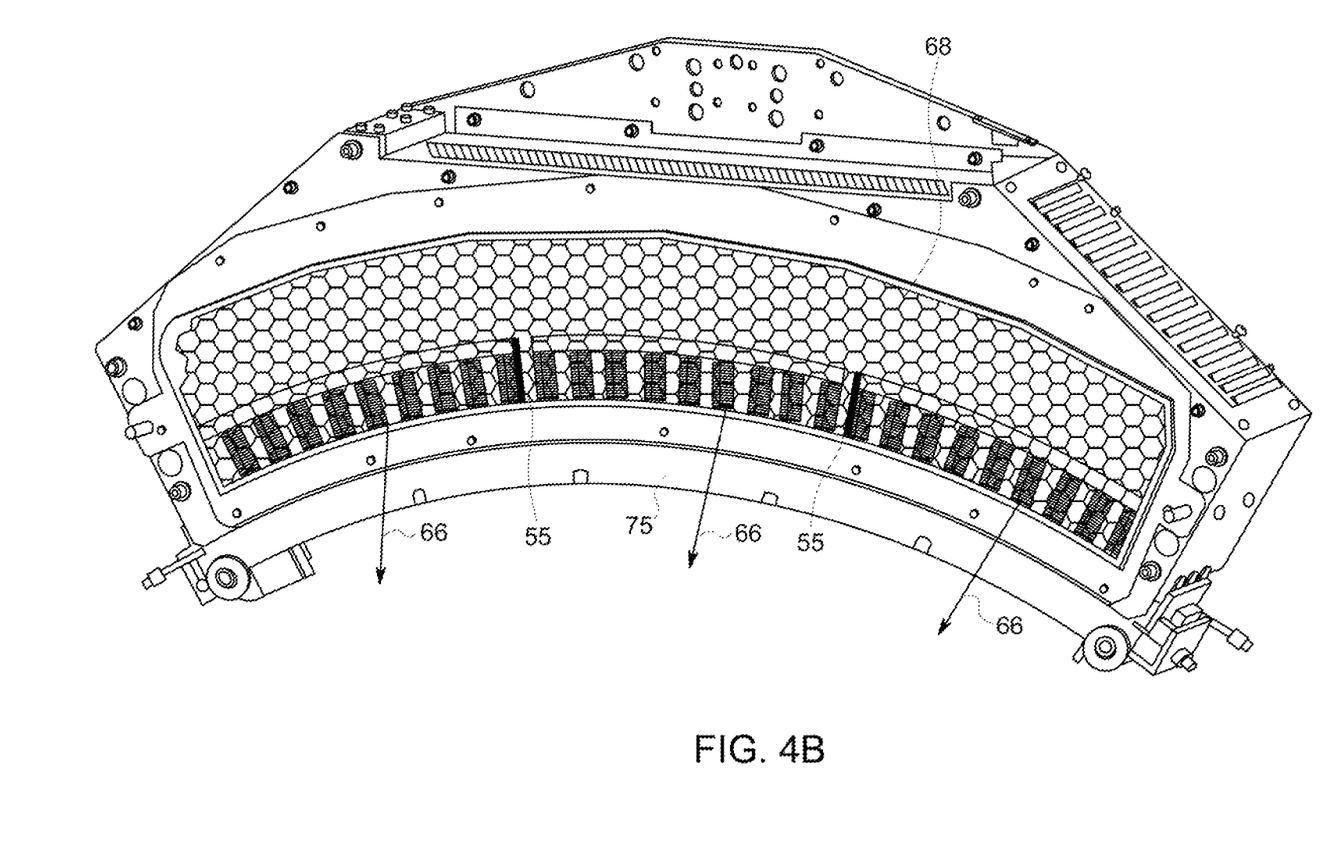

In the embodiment shown in FIGS. 4a and 4b, each zone 48-50 has at least one air intake 65 in the form of variable speed fan 51 and at least one air exit 66 in the form of vent 68. The system for thermal management 1 has a housing 69 with air intake ports 65 in the front and air exit ports 66 in the back. Each air intake port 65 may be associated with a fan, such as a variable speed fan 51-53. In alternative embodiments, several air intake ports 65 may be associated with a single fan or a single fan may be associated with several air intake ports 65. The system for thermal management 1 may comprise one or more detector rails 75. The detector rails may provide a mounting system for the detectors 57-59 and may also contain rail heaters 61-63 for each device for which the temperature is being managed. (See FIG. 5) In other embodiments, the rail heaters 61-63 and temperature sensors 71-73 may be mounted in any way so as to be in thermal connection with the detectors 57-59 so that heat from the rail heaters 61-63 may be transferred to the detectors 57-59.

Air exit 66 may be configured in any way to allow the air taken in by air intake port 65 to exit the system. In the embodiment of FIGS. 4a-4b, the air exit ports are on the back of the housing 69 running parallel to the front side having air intake port 65. FIG. 4b shows each air exit port 66 is separated by a flow patrician 55 that separates the zones from one another. The air exiting those air exit ports 66 is expelled through at least one vent 68 in the back of the system 1 that allows the air taken in by intake port 65 to exit the housing 69. Further each air exit port 66 may comprise one or more heat sinks to dissipate heat and help expel it from the system. The flow path of air through this embodiment of the system 1 is depicted and discussed in more detail with respect to FIG. 5.

In other embodiments, the air exit port may be positioned differently, such as on the top side of the housing 69 running perpendicular to the front side having the air intake port 65. In the embodiment of FIGS. 4a and 4b, the system for thermal management 1 has an arc shape conforming to the shape of the gantry 12. However, the system for thermal management 1 may take on any shape that is necessary or preferable for cooling the element device or devices.

As explained above, the embodiment of the system for thermal management 1 shown in FIGS. 3 and 4 has three zones 48-50. Each zone houses a detector 57-59, and also has at least one rail heater 61-63 for heating the detector and at least one temperature sensor 71-73 for monitoring the rail temperature. As explained above, each detector 57-59 may be an independent detector or may be a subdetector comprising part of a larger detector. Various embodiments of the system for thermal management 1 may comprise more than one temperature sensor and rail heater per zone. For example, in the embodiment shown in FIG. 5, each detector 57 is mounted on a pair of detector rails 75, and each of the pair of detector rails has at least one rail heater and one temperature sensor per zone. In other words, each zone has two rails running therethrough and each rail has at least one rail heater and one temperature sensor.

Figure 5:
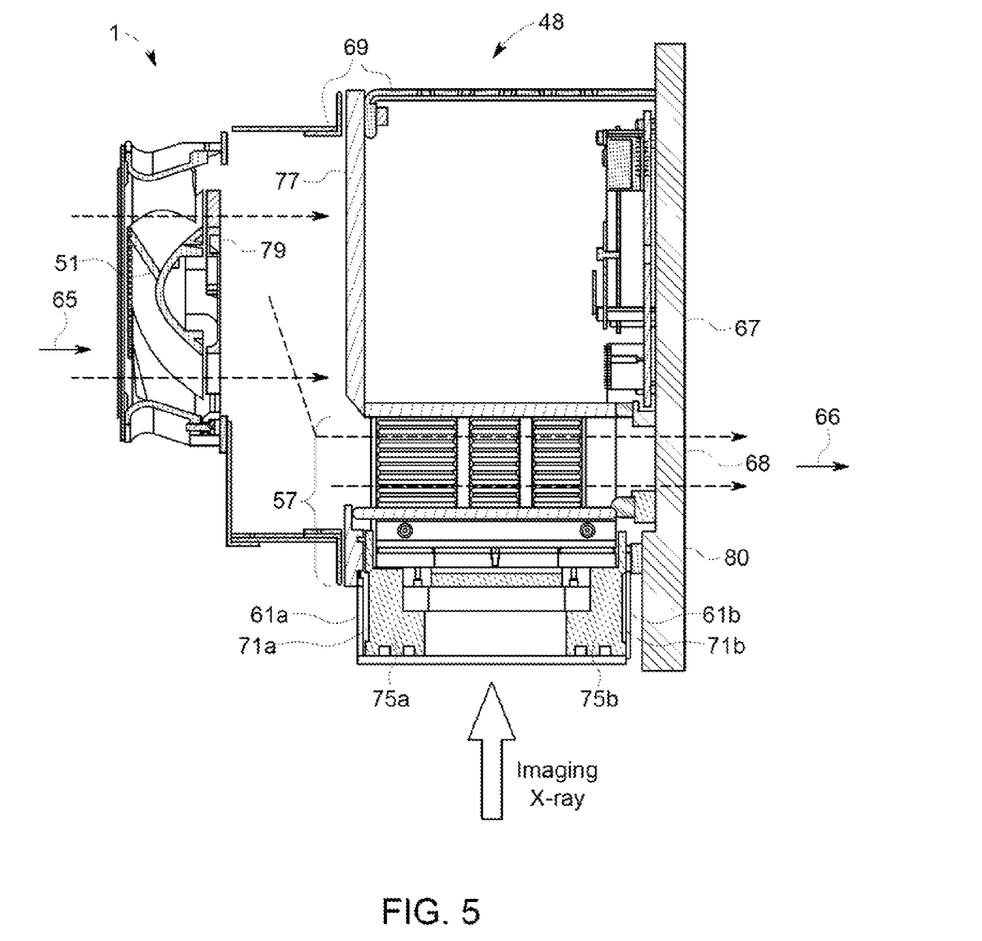
FIG. 5 provides a cut away view of an embodiment of a system for thermal management of a device.

FIG. 5 depicts a cut away view of a system for thermal management 1. The air flow through the device is depicted from the air intake point 65 to the air exit 66. The air enters the system through air intake port 65 propelled by variable speed fan 51. Diverter plate 77 diverts the air toward the detector 57. The air is then propelled out through the back side of the zone one 48 so that it exits the system through vent 68 in the DAS plate 67, which comprises the air exit 66. The DAS plate 67 may provide a mounting surface or it may house the DAS 32. In or around the air exit 66, such as in the vent 68, may include one or more heat sinks to absorb heat being expelled through the air exit 66. The embodiment of FIG. 5, which employs diverter plate 77, is configured to provide a maximum air flow across the detector 57 to create a maximum cooling efficiency and cooling, dynamic range of the detector 57. The goal of the thermal controls system design is to maximize the cooling control dynamic range to overcoming enable the widest possible change in thermal disturbances (such as inlet air temperature) while generating minimal audible noise and using minimal input power (maximize efficiencies) Other embodiments may employ other air-flow control devices to divert the air towards the detector. Alternatively, no diverter may be included, and the air may flow through the system from intake to exit without control by a diversion device.

The system may also include one or more air temperature sensors 79 to sense the temperature of the intake air into the system. The air temperature sensor(s) 79 may be placed at any location appropriate for providing functionally independent and unique feedback for controlling control actuators (fans and heaters). The embodiment of FIG. 5 has an air temperature sensor at the output of the variable speed fan 51. In other embodiments, the temperature sensor(s) 79 may be at or near the fan intake, or placed at the intake and exhaust whereby the temperature difference could be used as a control metric. In still other embodiments, the temperature sensor(s) 79 may be positioned somewhere between the fan and the detector. For example, the temperature sensor(s) 79 may be positioned on or near the diverter plate 77, or on or near some other device on the path between the fan and the detector.

As explained more thoroughly below, the speed of the variable speed fin 51 may be controlled based at least in part on the temperature of the intake air as measured by one or more air temperature sensors 79. The one or more air temperature sensors 79 may be any air temperature sensors known in the art and appropriate for measuring the temperature of the intake air as it flows into the system 1.

In the embodiment of FIG. 5, the detector system 57 is mounted to a pair of detector rails 75a and 75b. The detector rails of the embodiment of FIG. 5 comprise a pair of opposing rails 75a and 75b preferably made of a material with high thermal conductivity such as, for example, aluminum. Alternatively rail material may be selected for its low coefficient of thermal expansion such as 400 series stainless steels or invar. The detector rails 75a and 75b mount and support the detector 57 and are preferably conductive of heat and thus assist in the thermal management of the detector 57. The imaging x-rays are projected between the detector rails 75a and 75b onto the detector 57. The detector rails 75 may span across multiple zones, for example, across the three zones 48-50 depicted in FIGS. 3-4. In such an embodiment, the rails 75 may have thermal breaks therein, thermally isolating the detector rails 75 between zones. Alternatively, the detector rails may be continuous and may transfer heat from one zone to another. In still other embodiments, each zone may have its own detector rail(s) 75 which may be separate and isolated from the rail(s) of other zones.

The detector rails 75a and 75b may be associated with a heating system for heating the detector 57 if it falls below a predefined temperature. In the embodiment of FIG. 5, each of the detector rails 75a and 75b is fitted with a rail heater 61a and 61b and a temperature sensor 71a and 71b. Each rail temperature sensor 71a and 71b senses the temperature of the respective detector rail 75a and 75b. Rail heaters 61a and 61b act to heat the rails 75a and 75b, and thus to heat the detector 57.

The rail heaters 61-63 may be any heating devices appropriate for providing heat in the system 1. In a preferred embodiment, the rail heaters 61-63 may be flexible foil heaters where a resistive circuit is sandwiched between dielectric layers of materials. Kapton and Silicone are typical dielectric materials employed in flexible heater construction. In other embodiments, the rail heaters may include, but are not limited to cartridge style metal ceramic heaters or ceramic substrate heaters (typically direct conduction heaters are preferred as opposed to radiant heaters.

FIG. 3 demonstrates the embodiment depicted in FIGS. 4 and 5 shown in use in a CT imaging system 10. However, the system for thermal management 1 having multiple zones and controls as described herein, may be utilized in any system having multiple objects in an array that need temperature control. For example, the system for thermal management 1 may be employed in a positron emission tomography (PET) system or on analog/digital (A/D) boards in ultrasound devices.

In some embodiments, multiple air temperature sensors 79 may be utilized to determine the temperature of the intake air. For example, two or more temperature sensors may be placed in various locations along the intake port 65. The operation of the variable speed fan 51 may then be based on the output of the two or more air temperature sensors, for example using an average of the sensors. Such a system employing multiple air temperature sensors may help reject noise and thus yield a better control accuracy. Use of multiple sensors that are averaged have the advantage of reducing sensor error, location variability and enable continued operation in the case of a failed sensor be removing the sensor from the average.

Likewise, some embodiments of the system 1 may comprise multiple temperature sensors utilized to control the rail heaters 61a and 61b. For example, each detector rail 75a and 75b may have multiple temperature sensors, and the rail heaters 61a and 61b may be controlled based on an average temperature sensed by the multiple rail temperature sensors. In still other embodiments, temperature sensors may be associated with the detector 57, and the rail heaters 61a and 61b may be controlled in whole or in part based on the output of the one or more temperature sensors associated with the detector 57.

The temperature of the intake air determined by the sensor(s) 79 may be utilized to set the speed of the associated variable speed fan 51-53. The fans 51-53 of each zone 48-50 are operated independently. For example, the speed of one particular fan 51-53 may be increased if the air temperature increases, so as to provide more opportunity for convection and heat dissipation from the respective detector device 57-59. Alternatively or additionally, the speed of the variable speed fan 51-53 may be increased or decreased according to a device temperature measured by a temperature of the detector device 57-59 as measured by a device temperature sensor 80. For example, the fan speed may be increased as the respective temperature of the detector device 57-59 increases above a temperature setpoint or a predetermined temperature range for that detector. In other words, the speed of the variable speed fans 51-53 may be independently increased or decrease depending on how much the respective detector 57-59 needs to be cooled.

The control temperature setpoints can be a single constant value or the setpoint/s can have functional relationships to another input/feedback metric. An example of this would be to have the rail setpoint temperature made a linear function of air temperature thus producing a range of rail setpoints functionally related to inlet air temperatures at the fans. The setpoints used in the control design are selected based on required absolute and temperature change allowed for the x-ray sensor. Likewise, the rail heaters 61-63 of each zone 48-50 are operated independently of one another. The rail heaters 61-63 may each be controlled to turn on/off or increase/decrease their heating effect if the temperature of the rails and/or the detector fall below a predetermined temperature. In the embodiment of the exemplary zone 48 in FIG. 5, the rail heaters 61a and 61b may be operated independently of one another, or they may be operated simultaneously and equally. For example, the rail heaters 61a and 61b may be operated in response to the temperature measured by the rail temperature sensor 71a and 71b to maintain each of the rails at a predetermined temperature. Alternatively, another embodiment may contain only one rail temperature sensor 71, and each of the rail heaters 61a and 61b may be operated based on the temperature sensed by the single rail temperature sensor 71. In still other embodiments, the system 1 may contain only one rail heater 61 and/or may contain only one detector rail 75.

For example, the current to the controlled rail heater 61-63 may be increased depending on how much the respective detector device or rail needs to be heated. Thus, each rail heater 61-63 may be turned up or down (or simply on/off) based on the difference between the rail temperature sensed by the rail temperature sensors 71-73 and a rail temperature setpoint, which may be a fixed setpoint or a variable setpoint that is based on another feedback variables (such as inlet air temperature to the fan). Alternatively or additionally, the rail heaters 61-63 may be controlled based in whole or in part on the temperature of the respective detector device 57-59, such as based on the difference between the temperature measured by the device temperature sensor 80 and the device temperature setpoint. Alternatively or additionally, the rail heaters 61-63 may be controlled as a function of first air temperature in the plenum between the associated variable speed fan 51-53 and the associated detector 57-59. This may be measured by an additional air temperature sensor placed appropriately in the plenum space to measure the air temperature between the output of the associated variable speed fan 51-53 and the associated detector 57-59. Optionally, in such an embodiment, the rail heaters 61-63 may be controlled to be maintained within a predetermined range of a rail temperature setpoint, wherein the rail temperature setpoint is determined based on the measured plenum temperature, in another embodiment the rail setpoint could be made a function of the difference between the cooling air temperature and the module temperature.

Figure 6:
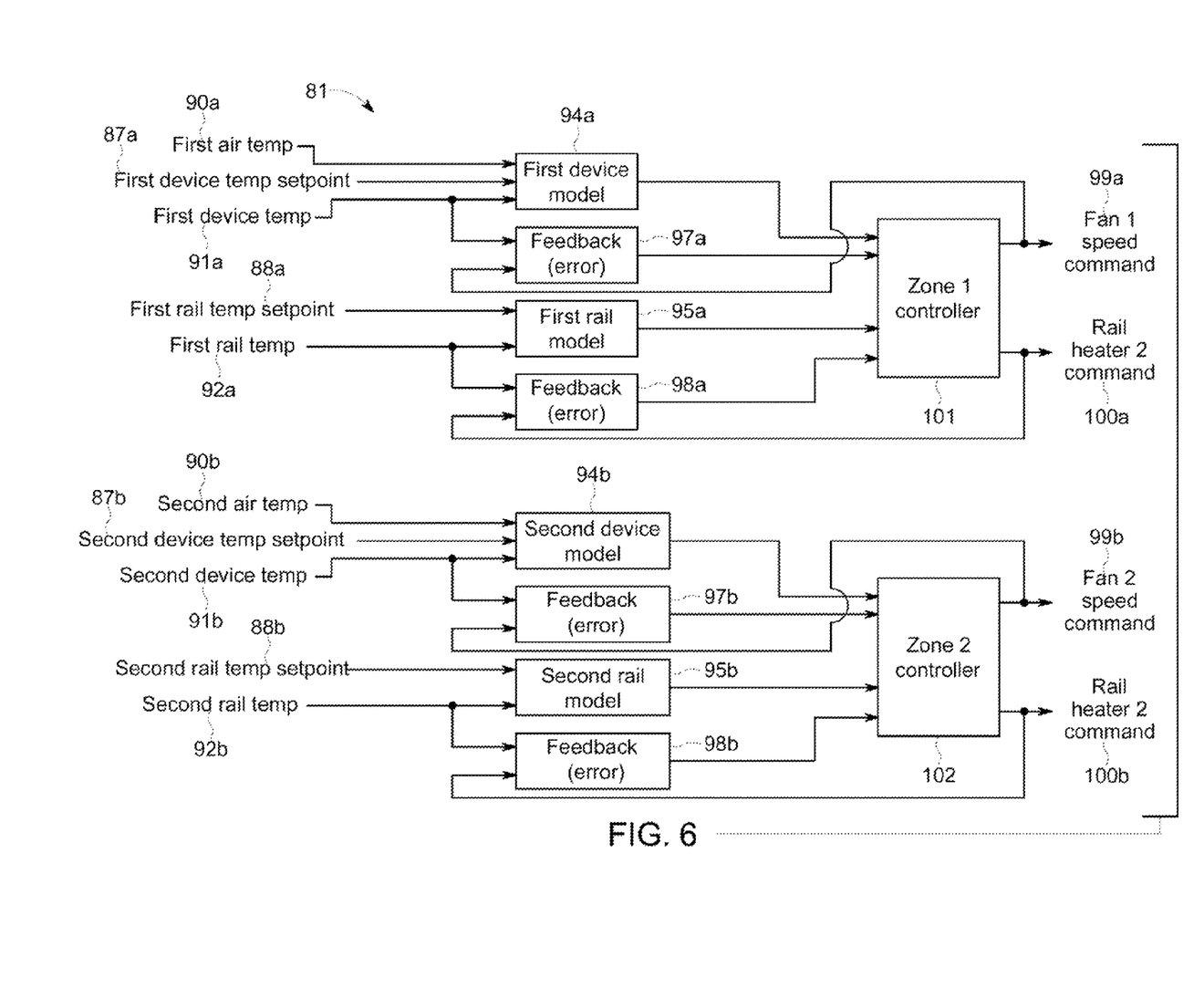
FIG. 6 depicts an exemplary system and method of thermal management.

An embodiment of the temperature control method and system 81 is shown in the block diagram of FIG. 6. In the depicted embodiment, two controllers, a zone one controller 101 and a zone two controller 102, are utilized to control the variable speed fan and rail heater of two separate zones. For the zone controlled by the zone one controller 101, the first air temperature 90a, a first device temperature 91a are supplied to a first device model 94a. The first device model 94a may be any digital model of the thermal behavior of the relevant detector device under specified operating conditions. For example, the first device model 94a may provide a numerical model of the first device under a particular set of air temperature and fan speed conditions, and thus may provide a model of the thermal behavior of the device over time given a certain start temperature, air temperature and fan speed. Thus, given a first air temperature 90a and a first device temperature 91a, the first device model 94a may provide an estimated fan speed for best achieving the first device temperature setpoint 87a.

The first device model 94a provides feed forward control information to the zone one controller 101. In other words, the first device model 94a provides information to the controller 101 based on knowledge of the device, such as a detector device 57-59, and how the device behave under certain conditions. The first device model 94a does not account for error between the estimate produced by the first device model 94a and the actual first device temperature 87a, nor does it account for any difference between the actual fan speed dictated by the fan speed command 99a and the actual fan speed achieved in the device. Such errors are accounted for by the feedback module 97a. The fan speed command 99a and the first device temperature 91a are provided to the feedback module 97a which calculates an error figure between an expected device temperature based on the fan speed command 99a and an actual device temperature 91a. The error calculated by the feedback module 97a is provided to the zone one controller 101, and the zone one controller 101 adjusts the estimate provided by the first device model 94a to account for the error in the system.

A similar process is carried out for controlling the rail heater. A first rail temperature setpoint 88a and a first rail temperature 92a are provided to a first rail model 95a. The first rail model 95a provides a mathematical model of the rail, or rails, in the relevant zone and associated with the relevant device. The first rail model 95a provides an estimated rail heater control command based on the first rail temperature 92a measured by a rail temperature sensor and a rail temperature setpoint 88a. In other words, the first rail model 95a provide an estimated command on how to maintain or achieve the first rail temperature setpoint 88a based on the measured conditions of the first rail.

As described above with respect to the fan speed controls, the zone one controller 101 may adjust the estimated command produced by the first rail model to account for the error calculated by the feedback module 98a to produce a rail heater command 100a. The feedback module 98a calculates the air between the rail heater command 100a and the actual temperature achieved as measured by a temperature sensor in the rail.

As shown in FIG. 6, a second zone controller 102 may operate identically, yet separately, from the first zone controller 101. The second zone controller 102 may output a fan speed command 99b and a rail heater command 100b to control a fan and rail heater associated with that zone. As described above, a second air temperature 90b, second device temperature setpoint 87b and second device temperature 91b are provided to a second device model 94b. The second device model calculates an estimated fan speed command based on those inputs and provides it to the zone two controller 102. The zone two controller 102 may adjust the estimated fan speed command based on feedback provided by the feedback module 97b. The associated fan or fans are then controlled by a fan speed command 99b which is output by the zone two controller 102.

Likewise, a second rail temperature setpoint 88b and a second rail temperature 92b are provided to a second rail model 95b. The second rail model 95b provides an estimated rail heater command to the zone two controller 102. That estimated command may be modified by the zone two controller 102 based on the error calculation provided by the feedback module 98b to provide a rail heater command 100b to an associated rail heater.

The zone one controller 101 and the zone two controller 102 may be any controller device capable of executing the control methods described herein. For example, the zone one controller 101 and the zone two controller 102 may each be a PID controller with antiwindup. Alternatively or additionally, the zone one controller 101 and the zone two controller 102 may include lead-lag compensators or optimal controllers. In still other embodiments, various other controllers may be implemented such as non-linear, adaptive, and robust controller schemes.

The zone one controller 101 and the zone two controller 102 may be part of a hierarchical control system, and thus a system controller may provide coordinated control between a zone one controller 101 and a zone two controller 102. For example, the system controller may engage in system management, such as to manage power, noise, vibration, etc., and may provide additional input to the zone one controller 101 and/or zone two controller 102 to modify the outputs thereof. Furthermore, the system controller may determine and/or account for disturbances in the larger system that may affect the thermal management of the respective zones. For example, the system controller may account for disturbances caused by rotation of the gantry during imaging operations. Alternatively or additionally, the system controller may account for disturbances between zones. For example, the system controller may calculate and/or account for disturbances in one zone caused by the operation of fans and/or rail heaters in another zone. To provide one example, such a disturbance may be a change in air pressure at the intake of a particular fan due to operation of an adjacent fan.

The system controller may receive input from sensors placed around the system in order to provide measurement input regarding disturbances. Alternatively, the system controller may operate based on system models and comparing the system models to the command produced by the various sub-controllers in the system, such as the exemplary zone one and zone two controllers 101 and 102.

In another embodiment, the zone one controller and/or the zone two controller may each account for disturbances in the system without the use of a system controller. Each of the zone one controller 101 or the zone two controller 102 may receive input from sensors placed around the system and configured to detect disturbances. Alternatively, the zone one controller 101 and/or the zone two controller 102 may incorporate or receive input from disturbance models, and may enter their output based on the input from the disturbance models. The disturbance modules or models may estimate the adjustment needed to the fan speed command or rail heater command in order to account for the measured or estimated disturbance. In still another embodiment, a decoupling scheme can be implemented that decouples the impact of the impacts from the activities in the other zones. The decoupling scheme may be static to single gain) or dynamic to dynamic equation).

In still other embodiments, the zone one controller 101 and the zone two controller 102 may be a single controller that controls the fan speed and rail heater of two or more separate zones. In such an embodiment, the single controller operates to control the fans and rail heaters of each zone independently from one another, such that the control methods described herein are executed separately for each zone.

Figure 7:
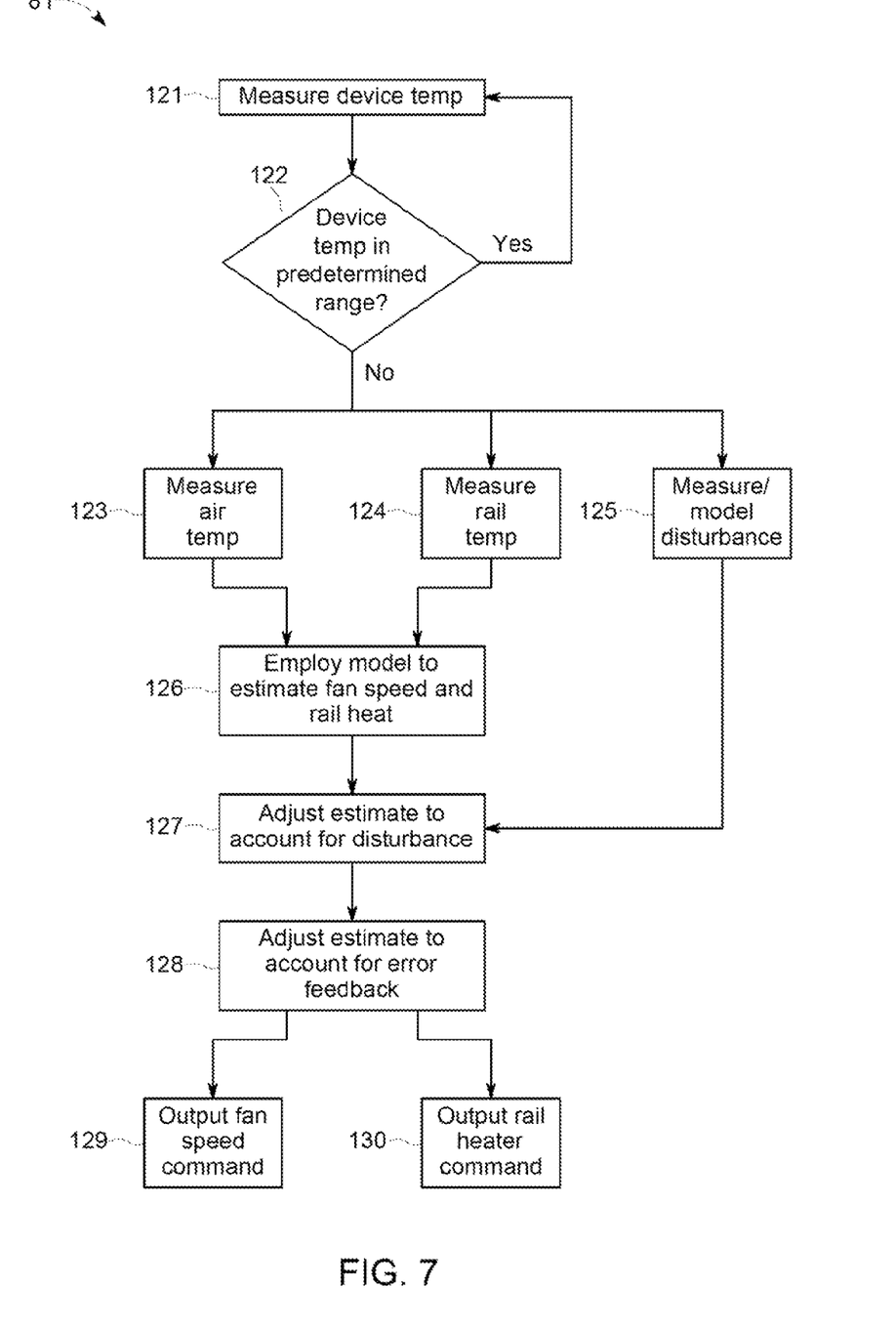
FIG. 7 depicts another exemplary method of thermal management.

FIG. 7 provides a flowchart schematic of a temperature control method 81 that may be used to control a fan and a rail heater in a particular zone. At step 121, a device temperature is measured, such as by a temperature sensor associated with a detector device. At step 122, a controller determines whether the device temperature is equal to a set temperature or within a predetermined temperature range. If the device temperature is equal to the set temperature or within the predetermined temperature range, then the controller loops back to monitor the device temperature until it deviates from the set temperature or falls out of the predetermined temperature range. Once the device temperature is not within the predetermined temperature range, the air temperature measurement 123, rail temperature measurement 124 and disturbance measurement or model 125 are provided as inputs. At step 126, device temperature models and rail models are employed, such as described above, to estimate the fan speed and a rail heater command. In some embodiments, a disturbance may also be accounted for at step 127. The disturbance may be accounted for based on a disturbance model or measurements at the actual disturbance taken at step 125 and provided as inputs to step 127. At step 128, the estimate may be further adjusted to account for error provided by a feedback module. Thereafter, an output fin speed command is provided at step 129 and an output error reader command is provided at step 130.

Figure 8:
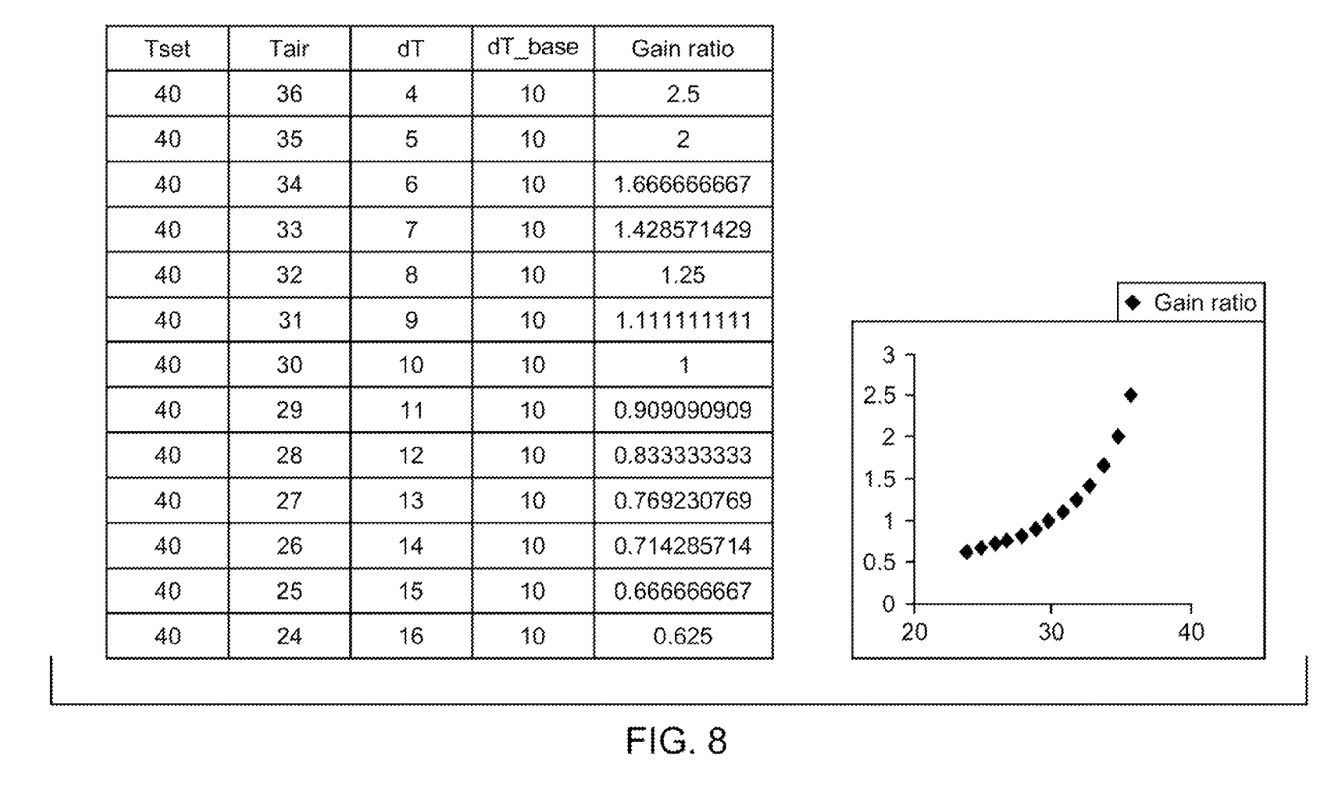
FIG. 8 depicts an exemplary gain schedule for an exemplary method of thermal management.

Alternatively or additionally, the controller may control the gain of the fan speed command or the rail heater command based on a gain schedule. The gain schedules may be devised based on a difference between measured temperatures, such as air temperature, rail temperature, or device temperature, and a temperature setpoint or predetermined temperature range. FIG. 8 provides an exemplary gain schedule for controlling a fan speed of one or more variable speed fans associated with a particular zone. As shown in the Figure, the gain ratio may vary proportionally to the difference in a measured air temperature ($T_{air}$) and a temperature setpoint ($T_{set}$). As can be seen from the chart in FIG. 8, as the difference (dT) between the set temperature and the air temperature increases, the gain ratio decreases.

In one embodiment, the fan controller executes the following control algorithm implementing a gain schedule such as that provided in FIG. 8. The objective is to minimize the temperature tracking error between the actual and setpoint outlet liquid temperatures. The system may employ a discrete PID control strategy with non-causal derivative and switching antiwindup as follows:

$$u_k = K_{DT}\left(e_k + \frac{1}{T_{iDT}}z_k + T_{dDT}\frac{e_k - e_{k-1}}{T_s}\right)$$

$$z_{k+1} = \begin{cases} z_k + e_u T_s & \text{if } FanMin \leq u_k \leq FanMax \\ z_k & \text{if } u_k < FanMin \text{ or } u_k > FanMax \end{cases}$$

$$e_k = Tdevice - Tdevice\_segment$$

In one embodiment, the proportional gain may be gain scheduled based on the plenum and device temperatures.

Alternatively, the controller may employ a causal derivative strategy with conditional antiwindup. In such an embodiment, the final fan speed control command is saturated and normalized, whereby:

$$D_k = \frac{1}{2\frac{T_f}{N} + T_s}\left(2T_f(e_k - e_{k-1}) - \left(T_s - 2\frac{T_f}{N}\right)D_{k-1}\right)$$

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system for thermal management in a CT device, the system comprising:
    a first thermal management zone comprising:
        a first x-ray detector;
        at least a first variable speed fan proximate to the first x-ray detector;
        a first air temperature sensor positioned to measure a first air temperature of the intake air to the first variable speed fan;
        a first rail heater in thermal contact with the first x-ray detector;
        a first rail temperature sensor in thermal contact with the first rail heater to measure a first rail temperature;
        a first controller that controls the first variable speed fan as a function of at least the first air temperature and the first rail heater as a function of at least the first rail temperature to maintain a temperature of the first x-ray detector within a predetermined range;
    at least a second thermal management zone comprising:
        a second x-ray detector;
        at least a second variable speed fan proximate to the second x-ray detector;
        a second air temperature sensor positioned to measure a second temperature of the intake air to the second variable speed fan;
        a second rail heater in thermal contact with the second x-ray detector;
        a second rail temperature sensor in thermal contact with the second rail heater to measure a second rail temperature;
        a second controller that controls the second variable speed fan as a function of the second air temperature and the second rail heater as a function of the second rail temperature to maintain a temperature of the second x-ray detector within the predetermined range; and
    a flow partition separating the first thermal management zone from the second thermal management zone.

2. The system of claim 1 wherein the first controller and the second controller are one controller that that controls the first variable speed fan as a function of the first air temperature sensor, the first rail heater as a function of the first rail temperature sensor, the second variable speed fan as a function of the second air temperature sensor and the second rail heater as a function of the second rail temperature sensor.

3. The system of claim 1 wherein the first controller and the second controller are linked by a system controller configured to coordinate functions of the first controller and the second controller.

4. The system of claim 1 wherein the first controller and the second controller are configured to vary gain based on operating conditions of the system.

5. The system of claim 4 wherein the first controller is configured to control a speed of the variable-speed fan by varying gain based on a difference between the first temperature of the intake air and the temperature of the first x-ray detector.

6. The system of claim 1 further comprising a third thermal management zone comprising:
- a third x-ray detector;
- a third variable speed fan proximate to the third x-ray detector;
- a third air temperature sensor positioned to measure a third temperature of the intake air to the third variable speed fan;
- a third rail heater in thermal contact with the third x-ray detector;
- a third rail temperature sensor positioned in thermal contact with the third rail heater to measure a third rail temperature; and
- a third controller that controls the third variable speed fan as a function of the third air temperature and the third rail heater as a function of the third rail temperature to maintain a temperature of the third x-ray detector within the predetermined range.

7. The system of claim 1 wherein at least one of the first zone or the second zone comprises multiple variable speed fans, wherein the multiple variable speed fans are controlled as a function of the first or second air temperature sensor to maintain the temperature of the first or second x-ray detection system within the predetermined range.

8. The system of claim 1 wherein the first air temperature sensor is positioned to measure a temperature of the intake air to the first variable speed fan and the second air temperature sensor is positioned to measure a temperature of the intake air to the second variable speed fan.

9. The system of claim 1 wherein the first air temperature sensor is positioned between the first variable speed fan and the first device, and the second air temperature sensor is positioned between the second variable speed fan and the second device.

10. A temperature control method, the method comprising:
- measuring the temperature of a first device with a first device temperature sensor disposed in thermal contact with the first device;
- disposing a first variable speed fan proximate to the first device;
- measuring a first air temperature with a first air temperature sensor disposed proximate the first variable speed fan;
- measuring a first rail temperature with a first rail temperature sensor disposed in thermal contact with a first rail heater;
- operating a first controller to control the first variable speed fan as a function of the first air temperature and to control the first rail heater as a function of the first rail temperature to maintain the temperature of the first device within a predetermined range;
- measuring the temperature of a second device with a second device temperature sensor disposed in thermal contact with the second device;
- disposing a second variable speed fan proximate to the second device;
- measuring a second air temperature with a second air temperature sensor disposed proximate the second variable speed fan;
- measuring a second rail temperature with a second rail temperature sensor disposed in thermal contact with a second rail heater; and
- operating a second controller to control the second variable speed fan as a function of the second air temperature and to control the second rail heater as a function of the second rail temperature to maintain the temperature of the second device within the predetermined range;
- wherein the first device and the second device are separated by a flow partition preventing air from flowing between the first device and the second device.

11. The method of claim 10 wherein the first controller further employs feed forward control based on a model of the thermal behavior of the first device under conditions including at least the first air temperature.

12. The method of claim 11 wherein the first controller further employs feed forward control based on the model of the thermal behavior of the first device under conditions further including at least the first rail temperature.

13. The method of claim 10 wherein the first controller further controls the first variable speed fan based on a gain schedule, wherein the gain schedule prescribes an incremental gain in fan speed based on the output of the first air temperature sensor and the first device temperature sensor.

14. The method of claim 10 wherein the predetermined range is +/−2 degrees from a temperature setpoint.

15. The method of claim 10 wherein the predetermined temperature range is +/−0.5 degrees from a temperature setpoint.

16. A system for thermal management of an imaging device, the system comprising:
- a housing defining at least two zones that are separated from each other, each zone having at least one air inlet and one air outlet, each zone comprising:
  - a variable-speed fan positioned near the air inlet;
  - an air temperature sensor positioned to measure a temperature of the intake air to the variable speed fan;
  - an x-ray detector;
  - a temperature sensor in thermal contact with the x-ray detector to measure the temperature of the x-ray detector;
  - a rail heater in thermal contact with the x-ray detector;
  - a flow diverter that directs an output of the variable-speed fan toward the x-ray detector;
  - a controller that controls the variable speed fan as a function of at least the air temperature and the temperature of the x-ray detector and controls the rail heater as a function of at least the temperature of the x-ray detector to maintain a temperature of the x-ray detector within a predetermined range.

17. The system of claim 16 wherein the controller further controls the rail heater as a function of the air temperature in a plenum between the variable speed fan and the x-ray detector.

18. The system of claim 16 further comprising a rail temperature sensor positioned in thermal contact with the rail heater to sense a rail temperature, and wherein the controller further controls the rail heater as a function of at least the temperature of the x-ray detector and the rail temperature.

* * * * *